United States Patent [19]

Mussi et al.

[11] Patent Number: 5,358,872
[45] Date of Patent: Oct. 25, 1994

[54] VESSEL AND CLOSURE ASSEMBLY

[75] Inventors: Edward F. Mussi, Hewitt; Harry E. Gray, Bloomingdale, both of N.J.

[73] Assignee: Becton, Dickinson and Company, Franklin Lakes, N.J.

[21] Appl. No.: 105,786

[22] Filed: Aug. 12, 1993

[51] Int. Cl.[5] .................. C12M 1/24; B65D 53/00
[52] U.S. Cl. .................... 435/296; 215/261; 422/102; 435/298
[58] Field of Search .............. 435/296, 298; 422/102; 215/226, 232, 248, 261, 270, 259, 307, 308, DIG. 3

[56] References Cited

U.S. PATENT DOCUMENTS

| | | | |
|---|---|---|---|
| 3,326,401 | 6/1967 | DeLong | 215/261 X |
| 3,870,602 | 3/1975 | Froman et al. | 435/296 |
| 4,142,940 | 3/1979 | Modolell et al. | 215/261 X |
| 4,289,248 | 9/1981 | Lynn | 215/330 |
| 4,377,247 | 3/1983 | Hazard et al. | 222/517 |
| 4,387,822 | 6/1983 | Lynn | 215/330 |
| 4,765,499 | 8/1988 | von Reis et al. | 215/24 |
| 4,770,308 | 9/1988 | Lynn | 215/330 |
| 4,935,371 | 6/1990 | Rickloff | 435/296 |
| 5,010,013 | 4/1991 | Serkes et al. | 435/296 X |
| 5,037,754 | 8/1991 | Tanaka et al. | 435/296 X |
| 5,047,347 | 9/1991 | Cline | 435/296 |

FOREIGN PATENT DOCUMENTS

| | | | |
|---|---|---|---|
| 0040797 | 12/1981 | European Pat. Off. | 215/226 |
| 1295468 | 5/1969 | Fed. Rep. of Germany | 251/261 |
| 2028082 | 8/1978 | United Kingdom | A01G 1/04 |

Primary Examiner—James C. Housel
Assistant Examiner—Arlen Soderquist
Attorney, Agent, or Firm—Nanette S. Thomas

[57] ABSTRACT

A vessel and closure assembly for culturing mammalian cells wherein a gas permeable membrane is provided in the closure to allow rapid and uniform equilibration of gases between the atmosphere of the vessel and the atmosphere of an incubator. Removable thin impermeable film labels are provided for allowing passage of gases through the gas permeable membrane for uniform equilibration between the atmosphere in the closure and the atmosphere of the incubator as well as for occluding passage of gases through the gas permeable membrane when the vessel is removed from the controlled atmosphere of the incubator.

10 Claims, 6 Drawing Sheets

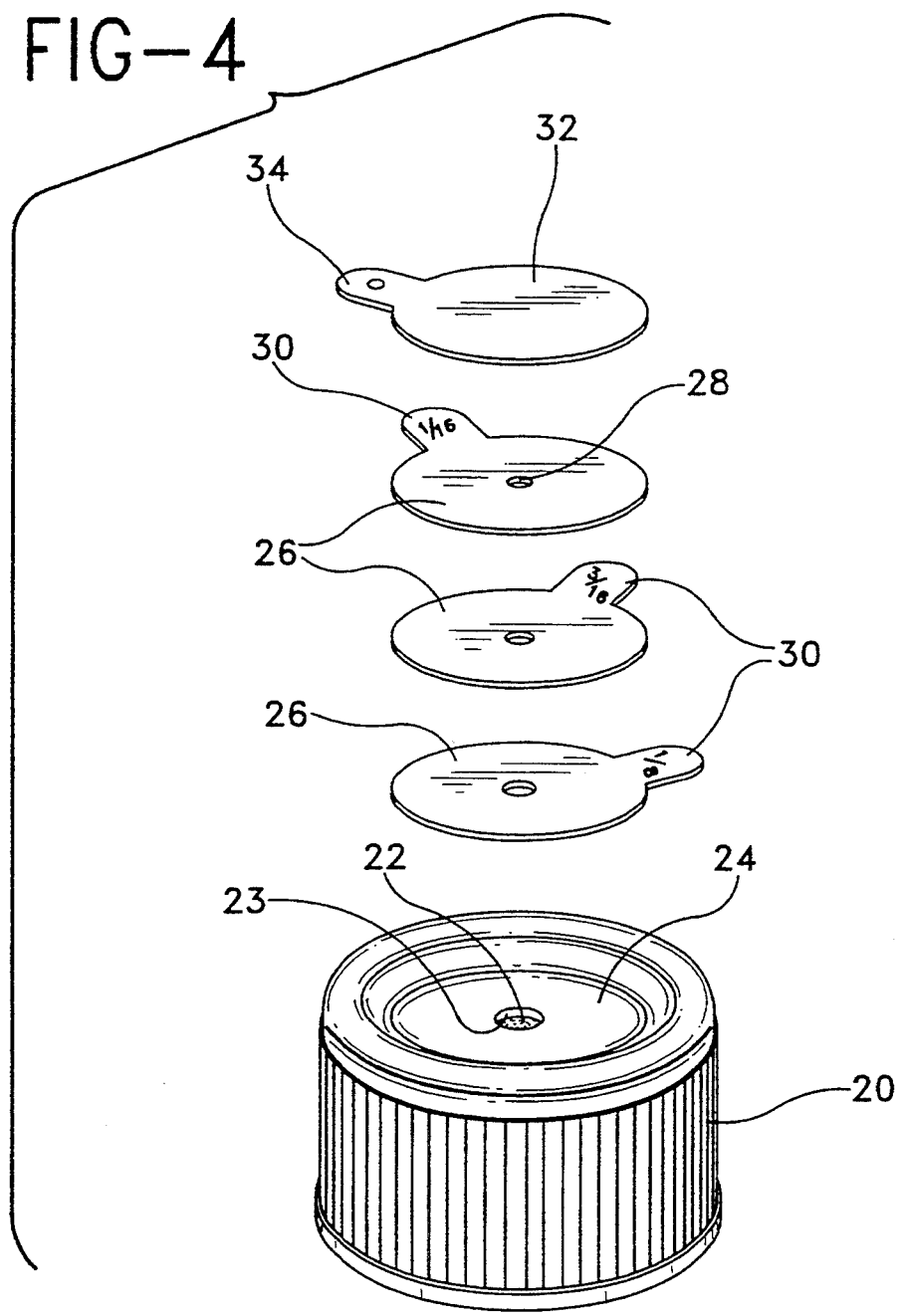

VESSEL AND CLOSURE ASSEMBLY

BACKGROUND OF THE INVENTION

1. Field of the Invention

This invention relates to a device for cell culture production, and more particularly to a vessel and closure assembly having means for varying the gas diffusion rate into and out of the vessel.

2. Description of Related Art

Typically, cells are cultured under conditions in which the hydrogen ion concentration (pH, the negative logarithm of the hydrogen ion concentration), temperature, humidity, osmolarity and concentration of certain ions are controlled within relatively narrow limits.

Vessels that are used in such tissue culture systems are typically made from plastic and include closures. Such vessels and closures are illustrated in U.S. Pat. Nos. 4,289,248, 4,387,822, 4,770,308 and 5,047,347.

In typical tissue culture systems, pH is maintained near physiologic levels by a buffering system in the tissue culture fluid, in conjunction with an incubator in which carbon dioxide ($CO_2$) is infused at a rate sufficient to maintain a concentration in the incubator atmosphere of approximately 5 to 7 volume percent. The $CO_2$ reacts with water to form the weak acid, carbonic acid, which in turn interacts with the buffering system to maintain the pH near physiologic levels. Entry of $CO_2$ from the incubator into the tissue culture vessel is generally achieved by utilizing a closure on the vessel such as, a loosely fitting cap, a stopper or a cap with a permeable membrane. Equilibrium in the vessel is maintained by allowing gas exchange with the inside of the vessel and the atmosphere of the incubator while preserving sterility and preventing liquid leakage. A loosely fitting cap or a stopper is partially opened to an approximate extent determined by the user or by the closure design.

Removal of the vessel from the controlled atmosphere of the incubator is often required during growth and culturing of cells. The vessels are usually removed for inspection and/or manipulation of the cells and culture fluids. It is important that the pH of the cell culture be maintained at the desired physiologic level while the vessel is outside of the incubator.

The limitations of the closures used with vessels for cell culturing such as those described in U.S. Pat. Nos. 4,289,248, 4,387,822, 4,770,308 and 5,047,347 are (1) susceptibility to contamination by microorganisms because of gas flow through the small but unobstructed space between cap and the vessel; (2) a slow and variable rate of achieving pH equilibration by diffusion of $CO_2$ through the loose-fitting cap and (3) the rate of gas exchange can not be estimated by a loose fitting cap or a cover that can be moved continuously without limitation.

A special need exists for an improved closure for a culture vessel which: (1) provides rapid and uniform equilibration between the vessel atmosphere and the incubator; (2) allows the culture vessel to be removed from the controlled atmosphere of the incubator for reasonably long times without subjecting the cell culture to undesirable changes in the pH of the system; (3) eliminates the guesstimated procedure of increasing and/or decreasing the gas exchange rate in order to substantially regulate the concentration of $CO_2$ inside the vessel; (4) provides a gas exchange rate that can be measured; and (5) provides precise control over the degree of venting.

SUMMARY OF THE INVENTION

The present invention is a vessel comprising a chamber, an opening, a closure or other means associated with the opening, means for allowing gas diffusion into and out of the vessel and means for selectively occluding the diffusion of gases. Most preferably, the closure seals the vessel.

Preferably the vessel is a flask, roller bottle, tube, spinner flask, stirred bioreactor or any vessel that is used in an incubator that requires gas exchange. Most preferably, the vessel is a flask or roller bottle.

Deskably, the closure is a cap, push cap, threaded cap, screw cap or a stopper. Most preferably, the closure is a cap.

Preferably, the closure comprises a top end with means for allowing gas diffusion into and out of the vessel. Preferably, the means for allowing the gases to be exchanged is a gas permeable membrane.

Further associated with the closure is a means for selectively occluding the membrane without disturbing the seal between the closure and the vessel. Preferably, the means for selectively occluding the membrane is a thin impermeable film with or without a gas restricting orifice. A thin film with no orifice may be removably attached to the top of the closure to restrict exposure of the microporous membrane to the atmosphere. Alternatively, a thin film with an orifice may be removably attached to the top of the closure to expose a portion of the membrane to the ambient atmosphere. The thin impermeable film does not disturb the seal between the closure and the vessel.

Most preferably, the means for selectively occluding the membrane is a series of thin impermeable films with graduated gas restricting orifices. The thin films are preferably peel-away impermeable labels wherein the labels may be removably superimposed over each other to cover the membrane so that the label nearest to the membrane has the largest orifice, and the label farthest away from the membrane has the smallest orifice or no orifice. As the specific cell culture procedure application requires, the labels may be peeled away in sequence during the course of the specific cell culture application or reapplied to cover the membrane.

Most preferably the labels are plastic with specific orifice dimensions wherein the dimension of the orifice may be marked on the label so that the user can select the level of gas exchange desired with substantial accuracy.

Preferred materials of the labels, include but are not limited to polymeric substrate resins that are impermeable to gases and liquids. The labels may be transparent or color coded as related to the dimension of the orifice. Printing may be placed on each label. For example, an orifice size identification. Moreover, the surface of each label may be such that additional information may be hand written on the label.

Although it is within the purview of the invention to have a series of labels, in the event a single specific gas exchange rate is required, without the need to vary the gas exchange rate, one label with the desired orifice may be used on the closure.

The labels are most preferably arranged on the top of the closure and superimposed over each other. The labels are arranged so that the orifices are in a graduated series wherein the label nearest to the membrane has the largest orifice and the label furthest away from the membrane has the smallest orifice or no orifice.

Although it is within the purview of the invention to have one or more than one label associated with the top of the closure, it is preferred that at least four labels be superimposed over each other on top of the closure to allow the user the flexibility of selecting the most accurate level of gas exchange in the vessel.

Most preferably, the first label which is removably attached to the top of the closure desirably comprises an orifice to expose a percentage of the surface area of the membrane, such as about 50% of the surface area of the membrane. A second label is removably attached to the first label and comprises an orifice dimension less than the orifice dimension of the first label to expose about 25% of the surface area of the membrane. A third label is removably attached to the second label and comprises an orifice dimension less than the orifice dimension of the second label to expose about 10% of the surface area of the membrane. Numerous labels can be used wherein the orifice dimension decreases as the number of labels increase. The fourth label is removably attached to the third label and has no orifice dimension or an orifice dimension less than the orifice dimension of the third label. The gas exchange rate in the vessel is directly proportional to the percentage of the surface area of the membrane exposed, and the selection of the appropriate orifice is dependent on the permeability of the membrane Alternatively, if the cell culturing application dictates, only one thin film may used to cover the membrane, containing no orifice so that initially a nearly gaslight seal is superimposed. During the time the vessel is in the incubator, and the specific culture procedure requires the entire membrane to be exposed to the atmosphere of the incubator, the label with no orifice, may be peeled away from the top of the cap to expose the membrane to the atmosphere. The use of only one label will not allow the user to gradually increase the rate of diffusion. However, the label that has no gas restricting orifice may be reapplied to cover the membrane when the vessel is removed from the controlled atmosphere of the incubator so that the vessel may be left outside the incubator for relatively long periods of time. Therefore, by covering the membrane with the label with no orifice, substantial escape of gases from the vessel is prevented and therefore undesirable changes in the pH of the culture does not result.

Although it is within the purview of the invention to provide labels that are circular having orifices that are circular, labels and orifices of different geometric configurations may be provided.

The labels allow rapid and uniform equilibration between the atmosphere in the vessel and the incubator so that the vessel atmosphere can be controlled to provide selected levels of gases (e.g. $CO_2$) that promote the desired growth of the cell culture while still providing a closed system that prevents entry of microbial organisms into the vessel. The labels do not compromise sterility or invite leakage into the vessel. Other advantages is that the labels are reusable and are economically feasible to manufacture.

The labels maximize gas exchange while minimizing the possibility of contamination. A further advantage is that gas exchange takes place exclusively through the membrane without having to partially open the vessel's cap and therefore sterility and leakage in the vessel are minimized. A further advantage is that the accuracy of controlling the gas exchange is substantially improved with the use of the labels. The predetermined size and dimension of the orifice allows the user to accurately approximate how much gas exchange will take place.

A further advantage of using labels with the membrane is that the need for a cap without a membrane is also eliminated.

A further advantage is that the labels ensure consistency of the product and also facilitate the production of multiple cell cultures for large scale production. Such large scale production applications often utilize transformed or partially transformed cell lines that overproduce $CO_2$ and lactic acid when grove to very high density in order to generate significant amounts of a commercial bioproduct, such as erythropoeitin (EPO) or tissue-type plasminogen activator (t-PA). In such large scale production applications wherein multiple vessels are required, each vessel in the production line can have the same amount of membrane exposed at the same time (obviating the need to guess the amount of vent to provide).

DETAILED DESCRIPTION

Figure 1:
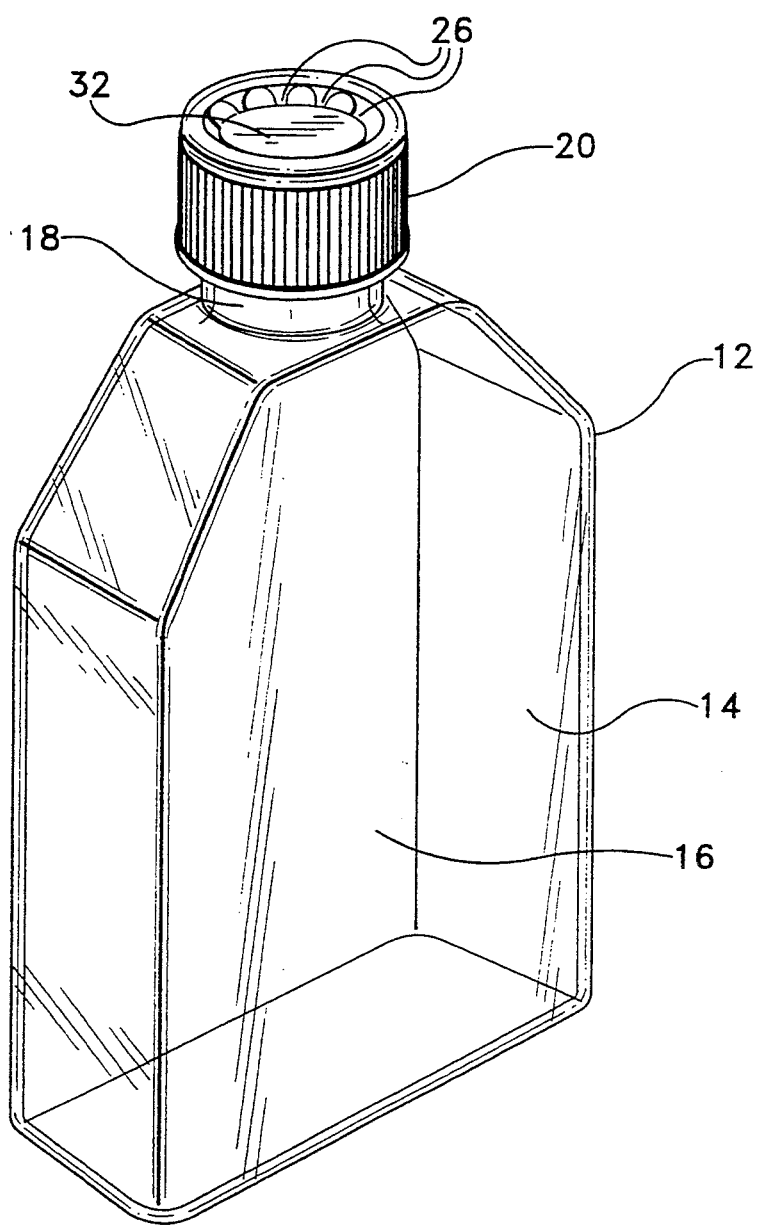
FIG. 1 is a perspective view of a flask with a cap comprising a gas permeable membrane and the preferred series of thin film labels of the present invention.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
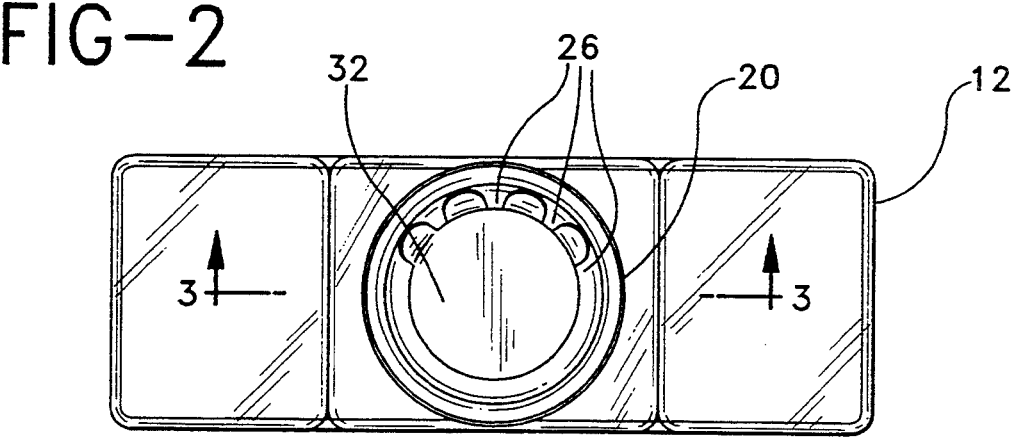
FIG. 2 is a top view of the flask and cap of FIG. 1.

FIGS. 1 and 2 illustrate a cell culturing vessel, flask 12, a cap 20 and peel-away thin impermeable film labels 26 and 32. The flask is preferably made from impact resistant plastic or glass which is gas impermeable, optically dear, non-toxic and inert with respect to the cells to be cultured.

Flask 12 has a body 14 that defines a chamber 16 in which material is adapted to be held until such time as the same is withdrawn or dispensed. It is unimportant whether body 14 is made of a collapsible or no-collapsible material, such as metals, plastics or glass.

Flask 12 includes a neck 18 which is threaded to receive cap 20. Neck 18 is integral with the flask and defines a cylindrical conduit having one end integral with the flask and the other end defining an opening through which the cells and culture fluids may be introduced into the body of the flask. Neck 18 and cap 20 constitute one of a number of well known means for introducing materials such as mammalian cells and culture fluids into chamber 16. As is conventionally know, cap 20 is unscrewed from neck 18 to provide an opening through which cells and culturing fluids can be introduced into the flask. The cap is subsequently screwed back onto the neck to re-seal the flask.

Figure 3:
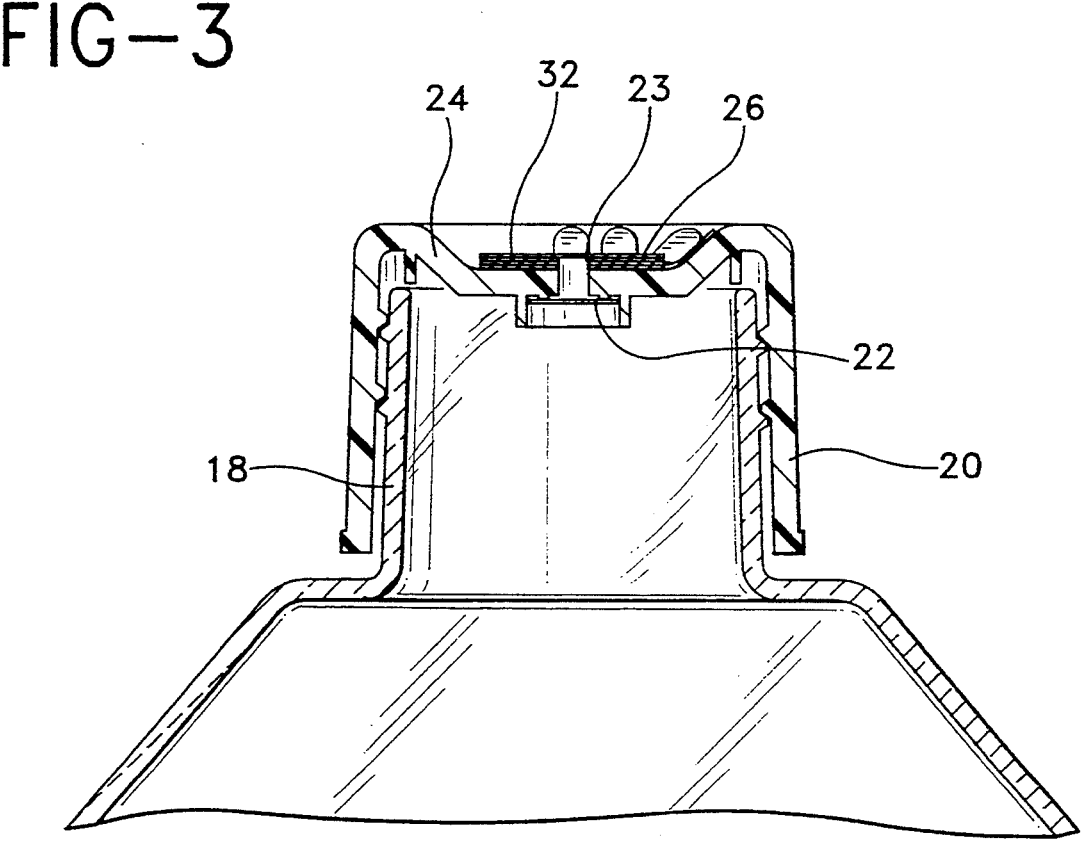
FIG. 3 is a cross-sectional view of the cap and thin film labels of FIG, 2 taken along line 3—3 thereof, FIG, 4 is a perspective view of the cap and series of thin film labels of FIG, 1.

As shown in FIG. 3, a gas permeable membrane 22 is associated with the orifice 23 of the top 24 of cap 20. The gas permeable membrane may be made from any suitable gas permeable material so long as it provides free passage of gases such as oxygen and carbon dioxide into chamber 16 while preventing bacteria and fungi from passing there through. Membrane materials provide adequate rates of carbon dioxide and oxygen permeability while preventing passage of microorganisms. Several gas-permeable materials having permeability sufficient to permit free passage of oxygen and carbon dioxide while preventing passage of bacteria and fungi are available. These materials include polyethylene, polycarbonate, acrylic co-polymers and polytetrafluoroethylene.

Peel-away thin film labels 26 are removably attached to the top of the cap and to each other so as to cover or selectively occlude the gas permeable membrane as the particular culture requires. Conventional means are used to apply the peel-away thin film labels to the top of the cap and to each other. These means include adhesive materials such as pressure sensitive materials, wherein the thin film labels can be easily and fully removed from the top of the cap or from each other as is required and reapplied if needed. The thin film label materials include polyethylene or polyethylene terephthalate and adhesive materials include acrylic adhesives.

As shown in FIG. 4, peel-away thin film labels 26 are circular, have an orifice 28, and a tab 30 and peel away thin film 32 has a tab 34 and no orifice. Although it is within the purview of the invention to provide peel away thin films that are circular and orifices that are circular, films and orifices of different geometries and dimensions may be provided.

The peel away thin film s are also marked with the dimension of the orifice for the particular film. As shown in FIG. 4, the first thin film or the thin film closet to the membrane has an orifice dimension of ⅛ inch, the second thin film has an orifice dimension of 3/32, the third thin film has an orifice dimension of 1/16, and the last thin film does not have an orifice and is marked as closed.

Figure 5:
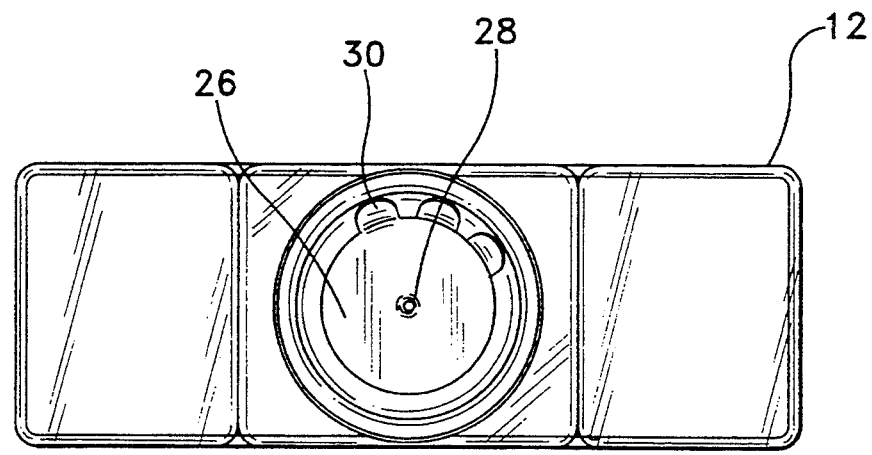
FIG. 5 is the top view of the flask and cap of FIG. 2 with the first thin film label removed from the top of the cap.

In use cap 20 is in the closed position when the flask is outside of the controlled atmosphere of the incubator. When flask 12 is placed within the controlled atmosphere of the incubator, the thin film or films are removed as shown in FIG. 5 to allow communication between the gases in the incubator atmosphere and chamber 16 to provide rapid and uniform equilibration.

Figure 6:
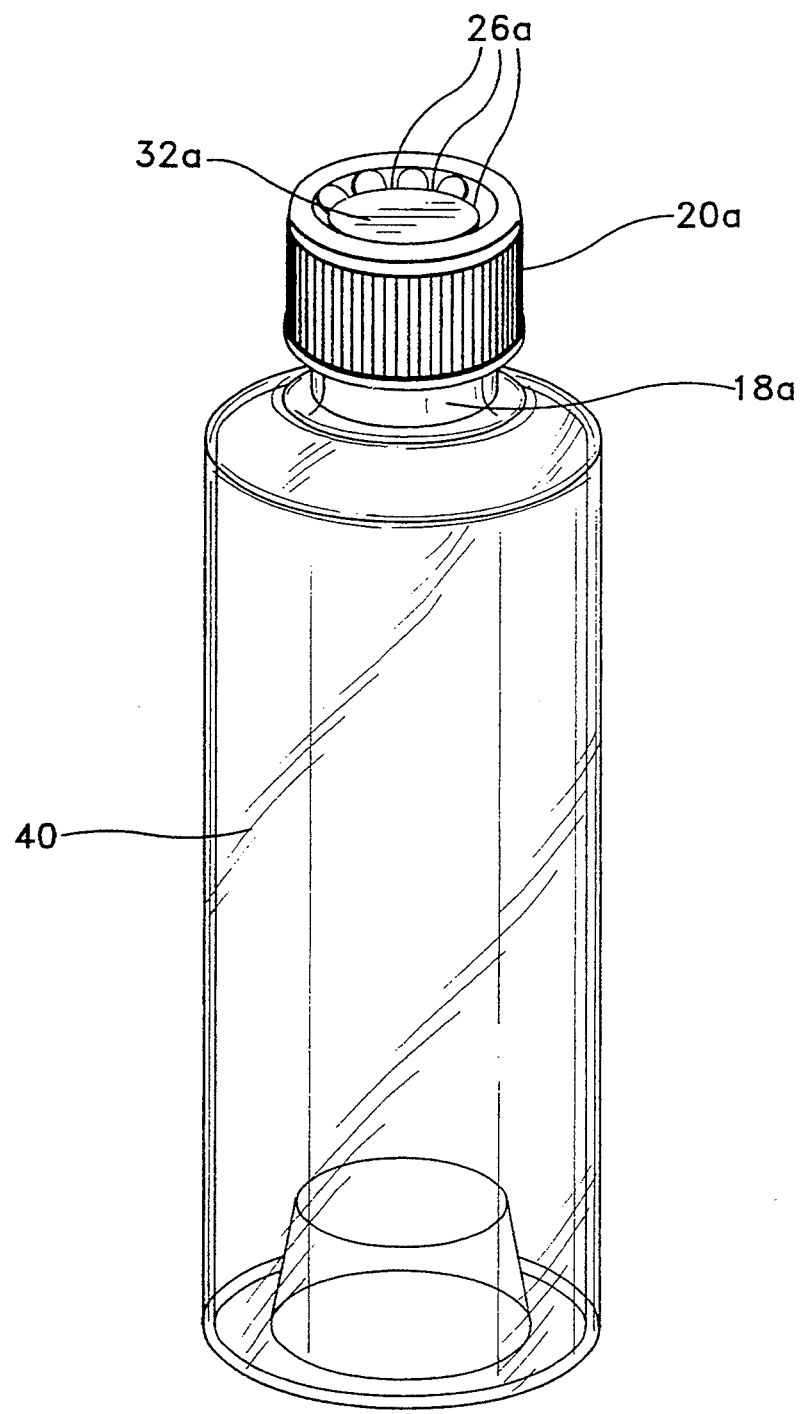
FIG. 6 is an alternate embodiment of the invention illustrating a perspective view of a roller bottle with a cap comprising a gas permeable membrane and the preferred series of thin film labels of the present invention.
Figure 7:
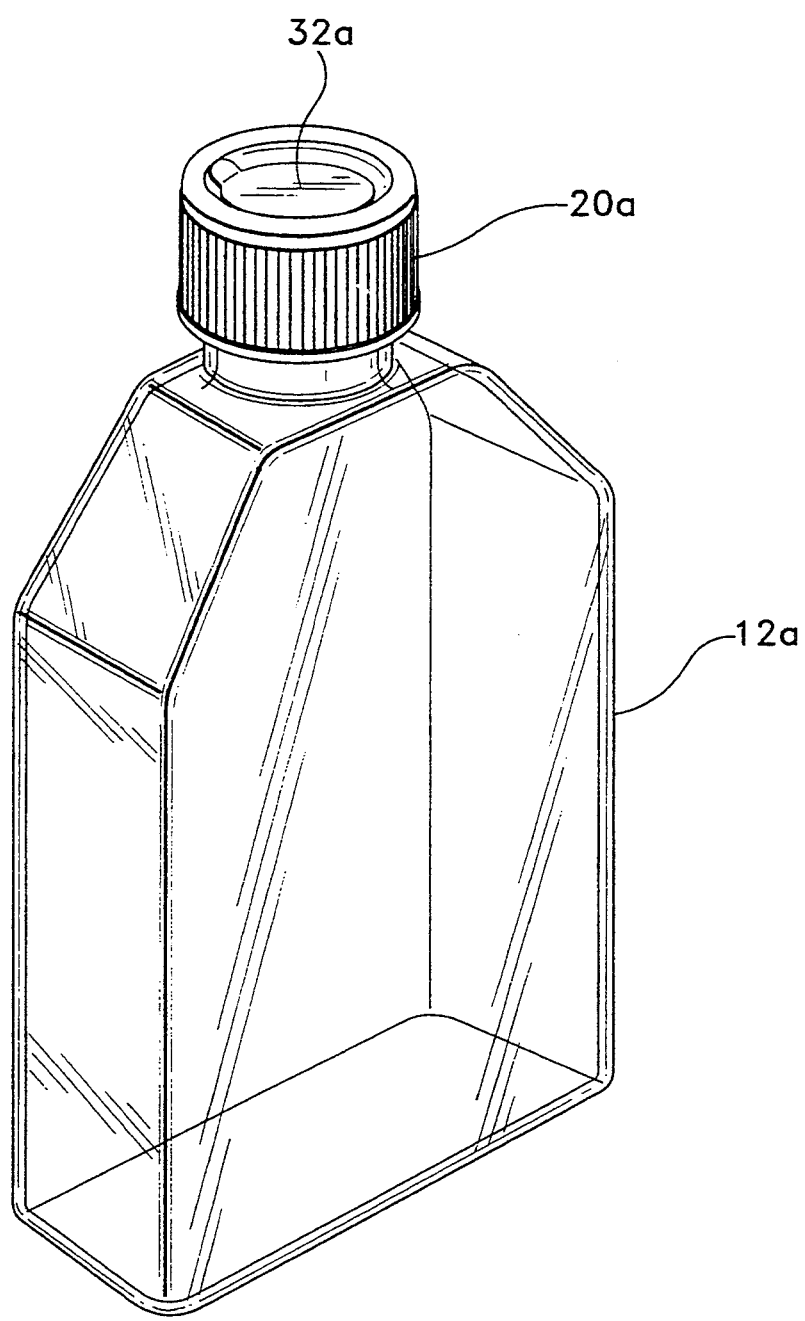
FIG. 7 is an alternate embodiment of the invention illustrating a perspective view of a flask with a cap comprising a gas permeable membrane and a thin film label with no orifice.
Figure 8:
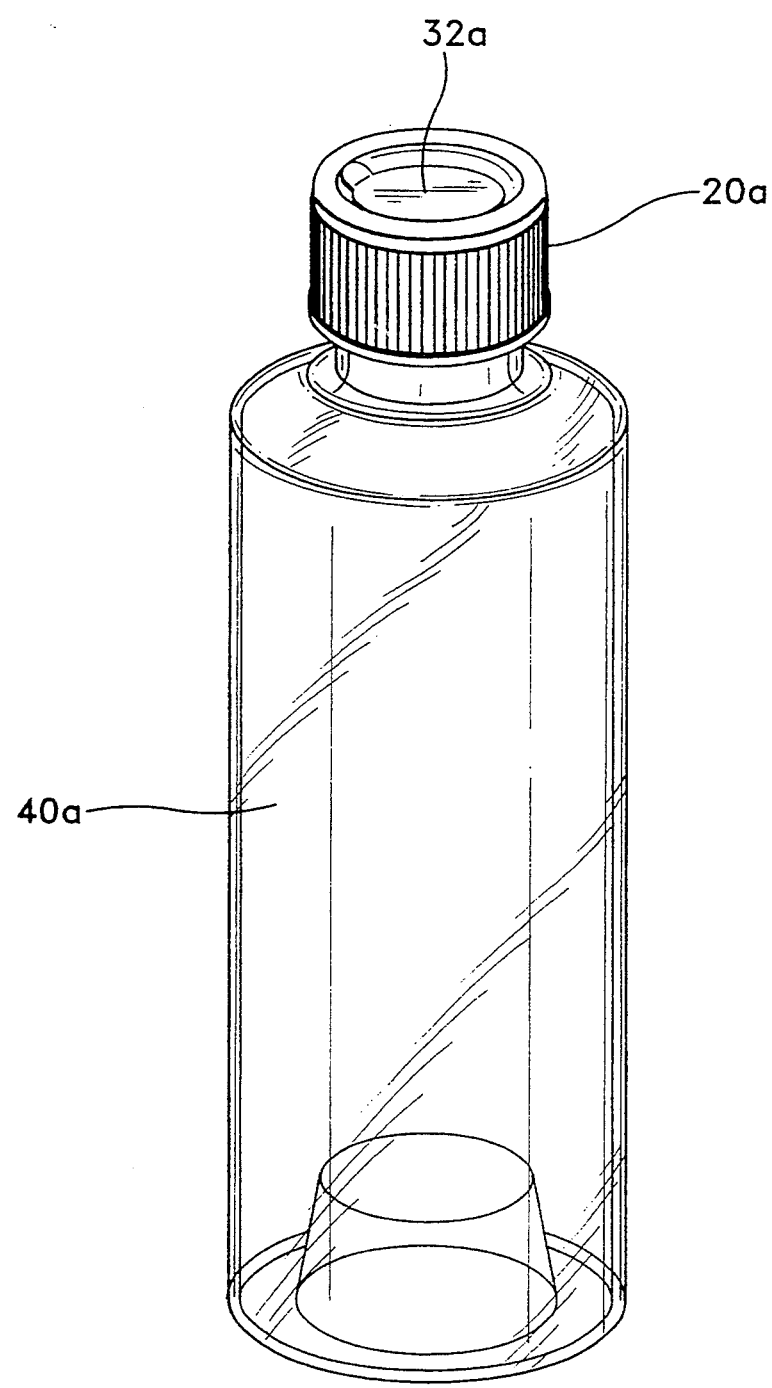
FIG. 8 is an alternate embodiment of the invention illustrating a perspective view of a roller bottle with a cap comprising a gas permeable membrane and a thin film label with no orifice.

The invention, as shown in FIGS. 6–8 includes many components which are substantially identical to the components of FIGS. 1–5. Accordingly, similar components performing similar functions will be numbered identically to those components of FIGS. 1–5, except that a suffix "a" will be used to identify those similar components in FIGS. 6–8.

Roller bottle 40 and cap 20a as shown in FIG. 6, is an alternate embodiment of a culture vessel system that can be used inside the controlled atmosphere of the incubator to provide rapid and uniform equilibration between the gases in the incubator and the vessel.

Alternate embodiments of the invention, as shown in FIGS. 7 and 8, is that one peel away thin film label 32a without an orifice is removably attached to the top of cap 20a.

Although the vessel in accordance with the present invention may have other uses with cell culturing systems in which gas permeability of the vessel is desired, the present invention is especially well suited for use in the constant carbon dioxide atmosphere incubators where it is desirable to allow the variable exchange of gases in the body of the vessel.

What is claimed is:

1. An assembly for use in growing cell cultures in incubators comprising:

a vessel comprising a body forming a chamber, a neck connected to said body having an opening for introducing cells and culture fluids into said chamber;

a closure for covering said opening in said neck comprising a top portion with an annular skirt extending from said top portion and having an inner surface and an outer surface and an orifice in said top portion with a means for removably mounting said closure to said neck, and means for allowing gases to be exchanged within said chamber; and a plurality of gas impermeable films removably superimposed over each other with one of said plurality of gas impermeable films being removably attached to said top portion of said closure wherein at least the gas impermeable film that is removably attached to said top portion has a gas restricting orifice for selectively occluding gas diffusion into and out of said vessel through the orifice in said top portion.

2. The assembly of claim 1 wherein said means for removably mounting said closure includes a threaded portion on said neck and a mating threaded portion on said skirt of said closure to provide screw type mounting of said closure to said neck.

3. The assembly of claim 1 wherein said vessel is a flask or a roller bottle.

4. The assembly of claim 3 wherein said vessel is a flask.

5. The assembly of claim 3 wherein said vessel is a roller bottle.

6. The assembly of claim 1 wherein said closure is a cap or a stopper.

7. The assembly of claim 1 wherein said means for allowing gases to be exchanged is a microporous membrane.

8. The assembly of claim 1 wherein at least two of said plurality of gas impermeable films have a gas restricting orifice of different size and are superimposed over each other to form a series of graduated gas restriction orifices.

9. The assembly of claim 1 wherein said gas impermeable films are peel-away labels removably superimposed over each other.

10. The assembly of claim 1 wherein said plurality of gas impermeable films comprise a first film having an orifice, a second film having an orifice smaller than the orifice of the first film, a third film having an orifice smaller than the orifice of the second film and a fourth film having no orifice, wherein said first film is removably superimposed over said top portion of said closure.

* * * * *